(12) United States Patent  
Kockx et al.

(10) Patent No.: US 9,391,394 B2  
(45) Date of Patent: Jul. 12, 2016

(54) MAGNETIC CONNECTOR ASSEMBLY

(71) Applicant: KONINKLIJKE PHILIPS N.V., Eindhoven (NL)

(72) Inventors: Franciscus Nicolaas Kockx, Tegelen (NL); Severin Luc Ramses Harvey, Utrecht (NL); Alexandra Petronella Maria Dermisek-Van De Langenberg, Dongen (NL); Pascal Ronald Treur, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/648,287

(22) PCT Filed: Dec. 3, 2013

(86) PCT No.: PCT/IB2013/060583  
§ 371 (c)(1),  
(2) Date: May 29, 2015

(87) PCT Pub. No.: WO2014/097034  
PCT Pub. Date: Jun. 26, 2014

(65) Prior Publication Data  
US 2015/0303619 A1    Oct. 22, 2015

(30) Foreign Application Priority Data

Dec. 21, 2012   (EP) ..................... 12198993

(51) Int. Cl.  
*H01R 13/60* (2006.01)  
*H01R 13/62* (2006.01)  
(Continued)

(52) U.S. Cl.  
CPC ............ *H01R 13/6205* (2013.01); *A61N 1/048* (2013.01); *A61N 1/0456* (2013.01); *H01R 13/03* (2013.01); *A61N 1/0492* (2013.01); *H01R 2201/12* (2013.01)

(58) Field of Classification Search  
CPC ............... H01R 13/6205; H01R 11/30; H01R 13/7037; H01R 13/53; H01R 13/2421; H01R 13/64; H01R 31/06; H01R 13/5224; H01R 24/58; H01R 2201/12; H01F 38/14; A61N 1/3752; A61B 5/0416  
USPC .............................................. 439/38, 39, 909  
See application file for complete search history.

(56) References Cited

U.S. PATENT DOCUMENTS 1,939,627 A * 12/1933 Lieber .................... H04R 27/02  
330/61 R  
4,004,298 A    1/1977 Freed  
(Continued)

FOREIGN PATENT DOCUMENTS

EP            2493029 A1    8/2012  
KR       2011120483 A    11/2011  
(Continued)

*Primary Examiner* — Abdullah Riyami  
*Assistant Examiner* — Vladimir Imas (57) ABSTRACT

There is provided a magnetic connector assembly comprising a first connector part (70) defining a first connection surface (82) and a second connector part (30) defining a second connection surface (38), the second connector part being connectable to the first connector part, wherein when the first connector part (70) and the second connector part (30) are connected they define a connection region over which the first connection surface (82) overlaps the second connection surface (38), such that an electrical signal may be transmitted between at least part of the first connection surface and at least part of the second connection surface in the connection region; and at least one of the first connector part (70) and the second connector part (30) comprises a magnet and at least the other of the first connector part and the second connector part comprises magnetisable material (74), such that when the first connector part and the second connector part are connected, the first and second connection surfaces (82, 38) are attracted to each other by a magnetic force; and wherein the first and second connector parts (70, 30) are arranged such that the magnetic force between the first and second connection surfaces (82, 38) is substantially weaker in a first part of the connection region than in a second part of the connection region.

13 Claims, 5 Drawing Sheets

(51) Int. Cl.
*A61N 1/04* (2006.01)
*H01R 13/03* (2006.01)

(56) References Cited

U.S. PATENT DOCUMENTS

| | | | |
|---|---|---|---|
| 4,112,941 A | 9/1978 | Larimore | |
| 4,653,503 A | 3/1987 | Heath | |
| 6,032,063 A * | 2/2000 | Hoar | A61B 5/04085 128/908 |
| 6,736,646 B2 * | 5/2004 | Takahashi | H01R 13/6633 439/39 |
| 6,897,370 B2 * | 5/2005 | Kondo | H02S 40/32 136/243 |
| 7,066,739 B2 * | 6/2006 | McLeish | H01R 13/6205 439/39 |
| 7,104,801 B1 * | 9/2006 | Brodnick | H01R 11/22 439/38 |
| 7,311,526 B2 * | 12/2007 | Rohrbach | H01R 13/6205 439/218 |
| 7,341,458 B1 * | 3/2008 | Koh | H01R 13/2421 439/39 |
| 7,351,066 B2 * | 4/2008 | DiFonzo | H01R 13/641 439/39 |
| 7,637,747 B2 * | 12/2009 | Jaatinen | A61B 5/0408 439/39 |
| 7,873,772 B2 * | 1/2011 | Waldhoff | A61B 5/0002 439/38 |
| 8,105,091 B2 * | 1/2012 | Nishihira | H01R 13/6205 439/39 |
| 8,696,366 B2 * | 4/2014 | Chen | H01R 13/6205 439/39 |
| 8,734,165 B2 * | 5/2014 | Neel | H01R 11/30 439/39 |
| 8,794,980 B2 * | 8/2014 | McCormack | H01R 13/6205 439/39 |
| 2003/0195587 A1 | 10/2003 | Rigaux et al. | |
| 2007/0072442 A1 | 3/2007 | DiFonzo et al. | |
| 2011/0171837 A1 | 7/2011 | Hardisty et al. | |
| 2012/0252231 A1 | 10/2012 | Kall | |
| 2015/0303619 A1 * | 10/2015 | Kockx | A61N 1/048 607/149 |

FOREIGN PATENT DOCUMENTS

| | | |
|---|---|---|
| WO | 0103768 A1 | 1/2001 |
| WO | 02089911 A1 | 11/2002 |
| WO | 2011151742 A1 | 10/2011 |

* cited by examiner

MAGNETIC CONNECTOR ASSEMBLY

CROSS-REFERENCE TO PRIOR APPLICATIONS

This application is the U.S. National Phase application under 35 U.S.C. §371 of International Application No. PCT/IB2013/060583, filed on Dec. 3, 2013, which claims the benefit of European Patent Application No. 12198993.3, filed on Dec. 21, 2012. These applications are hereby incorporated by reference herein.

TECHNICAL FIELD OF THE INVENTION

The invention relates to a magnetic connector assembly comprising a first part and a second part connectable to the first part, and in particular relates to a magnetic connector assembly which connects an electrode for attachment to a subject's body to a connector of a medical device.

BACKGROUND TO THE INVENTION

Physiological electrodes attached to the skin of a subject can receive electrical signals generated by the human body, which are then used to monitor physiological functions (such as heart rate and muscle activity), and/or can deliver electrical signals to the body, for example to stimulate muscle contraction or relieve pain.

Figure 1:
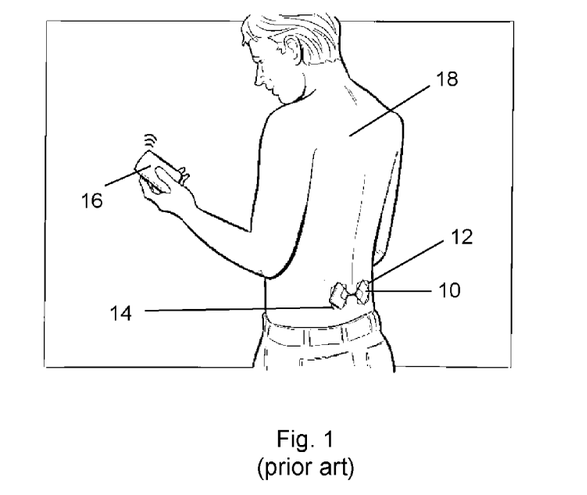
FIG. 1 shows a prior art TENS system in use.

For example, transcutaneous electrical nerve stimulation (TENS) is a technique in which electric current is applied to a body part of the subject via two or more skin mounted electrodes. TENS treatment typically requires electrical current to be applied to the body for a significant amount of time each day, including while the subject goes about their daily activities. In wireless TENS, a TENS device (which generates the electrical current) is placed directly on an electrode attached to the skin of a subject. FIG. 1 shows a wireless TENS system comprising a TENS device 10, two electrodes 12, 14 and a remote control 16 being used to treat the lower back of a subject 18. It is preferable for the TENS device to be very limited in size to prevent hindering of movement and to ensure comfort when worn under clothing. Construction height of TENS devices is therefore a very important factor, which is significantly influenced by the type of connector used to connect the TENS device to the electrode.

Additionally, it is a key benefit for the TENS user to be able to easily connect and disconnect the TENS device from the electrode, thus facilitating placement of the device on electrodes in difficult to reach body positions (e.g. the back). An easy-to-use connector is also necessary for subjects who have reduced use of their hands and fingers (for example because they suffer from osteoarthritis).

Known skin electrodes, including those used for TENS, are typically connected to a medical device (such as a TENS device) using a mechanical connection. For example, a typical electrode has a male snap structure configured to engage in a snap-fit connection with a female receiving portion of the medical device connector. As such, force is required to connect and disconnect the electrodes from the medical device connector. This makes such connectors difficult to use by people who are unable to easily apply the required amount of force. It also makes connection to electrodes located on soft body parts (such as the stomach) very difficult or impossible, since such body parts do not provide a firm support to press against. It also makes connection to electrodes located on painful body parts (for example which have been injured) unpleasant; since the force which needs to be applied may cause further pain and discomfort.

These difficulties of connecting the medical device connector and the electrode may lead to improper connections, reducing the effectiveness of the treatment or monitoring being carried out by means of the medical device.

To mitigate these issues, the use of magnetic connectors to connect medical devices to electrodes has been proposed. WO2011/151742, for example, describes an electrode assembly comprising an electrode and a connector, in which a connection between the electrode and connector is formed by way of a magnet provided in the connector assembly magnetically coupling to a magnet or magnetized material in the electrode.

U.S. Pat. No. 4,112,941 A discloses a connector assembly with a connector containing a magnet and a hole for mating with an elongated upstanding contact member of an electrode. An additional clearance is provided in the hole to allow for an unhindered intentional disconnection of the connector from the electrode.

KR 2011 0120483 discloses a terminal connection module comprising a first connection body with a magnetic part and a second connection body with a corresponding magnetic part that is connectable to the first magnetic part. When connected, terminal parts in the first and second body electrically contact each other.

US 2011/171837 shows a connector system with a plurality of magnetic elements arranged around a first and a second cable, respectively. Furthermore, at least one guiding element may be configured to orient the cables correctly.

SUMMARY OF THE INVENTION

The present invention provides a first connector part according to claim 1, and a second connector part according to claims 7 and 9. Preferred embodiments are disclosed in the dependent claims.

According to a first aspect of the invention, there is provided a magnetic connector assembly comprising a first connector part defining a first connection surface and a second connector part defining a second connection surface, the second connector part being connectable to the first connector part, wherein when the first connector part and the second connector part are connected they define a connection region over which the first connection surface overlaps the second connection surface, such that an electrical signal may be transmitted between at least part of the first connection surface and at least part of the second connection surface in the connection region; and at least one of the first connector part and the second connector part comprises a magnet and at least the other of the first connector part and the second connector part comprises magnetisable material, such that when the first connector part and the second connector part are connected, the first and second connection surfaces are attracted to each other by a magnetic force; and wherein the first and second connector parts are arranged such that the magnetic force between the first and second connection surfaces is substantially weaker in a first part of the connection region than in a second part of the connection region.

In order to provide a sufficiently strong connection to maintain good electrical contact between the first and second connector parts of a magnetic connector assembly in, for example, a TENS system, and to ensure that accidental disconnection cannot easily occur, it is desirable that the overall magnetic force between the first and second connector parts be as strong as possible. However, this must be balanced against the need for the user to be able to easily disconnect the first and second connector parts when desired. Embodiments of the claimed invention advantageously enable a magnetic connector assembly in which the overall magnetic force between the first and second connector parts is particularly strong, because they provide a local weakening of this magnetic force. Because this local weakening is experienced only when a disconnecting force is applied, for example, at a particular location and/or in a particular direction, the resistance of the connector assembly to accidental disconnection is not significantly affected. The ease by which a user, who knows the optimum manner in which to apply a disconnection, can separate the first and second connector parts is, however, significantly improved. Consequently a stronger magnet can be employed by the magnetic connector assembly, which improves the electrical contact and reduces the risk of accidental disconnection.

The first connector part and the second connector part may be arranged such that, when connected, the separation between the magnet and the magnetisable material is greater at a first point corresponding to the first part of the connection region than at a second point corresponding to the second part of the connection region. The magnetic connector assembly may be arranged such that the difference between the magnetic force between the first and second connection surfaces in the first part of the connection region and the magnetic force between the first and second connection surfaces in the second part of the connection region is at least 2 Newtons.

One of the first and second connection surfaces may comprise a protrusion arranged to engage with a corresponding recess on the other of the first and second connection surfaces so as to substantially prevent relative lateral movement between the first and second connection surfaces whilst permitting relative rotation thereof.

The invention further provides, according to a second aspect, a first connector part connectable to a second connector part such that an electrical signal may be transmitted therebetween, the first connector part comprising: a first connection surface arranged to be engageable with a corresponding second connection surface on a second connector part such that an electrical signal can be transmitted between the first connection surface and the second connection surface; and a target comprising magnetisable material; wherein the first connector part is characterized by being arranged such that, when exposed to a substantially uniform magnetic field, the magnetic force experienced by a first area of the connection surface is substantially weaker than the magnetic force experienced by a second area of the connection surface.

The first area of the connection surface may be located adjacent to an edge of the connection surface. The first connector part may be arranged such that a surface of the target forms at least part of the connection surface. The first connector part may be arranged such that the target additionally comprises a non-magnetisable material, and such that the first area of the first connection surface corresponds to the part of the target which comprises a non-magnetisable material and the second area of the connection surface corresponds to the part of the target which comprises a magnetisable material.

The shape of the portion of the target which comprises magnetisable material may be asymmetric with respect to the center of the first connection surface, such that the amount of magnetisable material contained in the volume of the first connector part immediately below a first half of the first connection surface is greater than the amount of magnetisable material contained in the volume of the first connector part immediately below the second half of the first connection surface, and wherein the first area of the first connection surface is contained within the second half. The portion of the target which comprises magnetisable material may have a non-uniform thickness in a direction perpendicular to the connection surface, such that the amount of magnetisable material contained in the volume of the first connector part immediately below a first half of the first connection surface is greater than the amount of magnetisable material contained in the volume of the first connector part immediately below the second half of the first connection surface, and wherein the first area of the first connection surface is contained within the second half.

The first connector part may further comprise a layer of flexible material having an attachment surface arranged to attach to a body tissue of a subject such that an electrical signal may be transmitted between the attachment surface and the body tissue; wherein at least part of the attachment surface is electrically connected to the first connection surface, and wherein the layer of flexible material and the target are fastened together in a sandwich arrangement by a pin.

The invention further provides, according to a third aspect, a second connector part connectable to a first connector part such that an electrical signal may be transmitted therebetween, the second connector part comprising: a second connection surface arranged to be engageable with a corresponding first connection surface on a first connector part such that an electrical signal can be transmitted between the second connection surface and the first connection surface; and a magnet comprising magnetic material; wherein the second connector part is characterized by being arranged such that the magnetic field strength at a first area of the second connection surface is substantially weaker than the magnetic field strength at a second area of the second connection surface.

The shape and/or location of the magnet may be asymmetric with respect to the center of the second connection surface such that the amount of magnetic material contained in the volume of the second connector part immediately below a first half of the second connection surface is greater than the amount of magnetic material contained in the volume of the second connector part immediately below the second half of the second connection surface, and wherein the first area of the second connection surface is contained within the second half. The second connector part may be arranged such that a first portion of the magnet which corresponds to the second area of the second connection surface comprises the magnetic material and a second portion of the magnet which corresponds to the first area of the second connection surface comprises a further, different, magnetic material, and wherein the magnetic field generated by the magnetic material is stronger than the magnetic field generated by the further magnetic material.

The second connector part may further comprise a magnet housing which at least partially surrounds the magnet and forms at least part of the second connection surface. The magnet housing may partially comprise a magnetically transparent material and may partially comprise a magnetisable material such that the part of the magnet housing which comprises a magnetisable material forms the first area of the second connection surface and the part of the magnet housing which comprises a magnetically transparent material forms the second area of the second connection surface. The magnet housing may be shaped such that the separation between the magnet and the second connection surface is greater at a first point corresponding to the first area of the second connection surface than at a second point corresponding to the second area of the second connection surface.

The magnetic material may comprise neodymium.

The invention further provides, according to a fourth aspect, a transcutaneous electrical nerve stimulation apparatus (20) comprising the magnetic connector assembly as described above; and/or the first connector part as described above; and/or the second connector part as described above.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION

Figure 2:
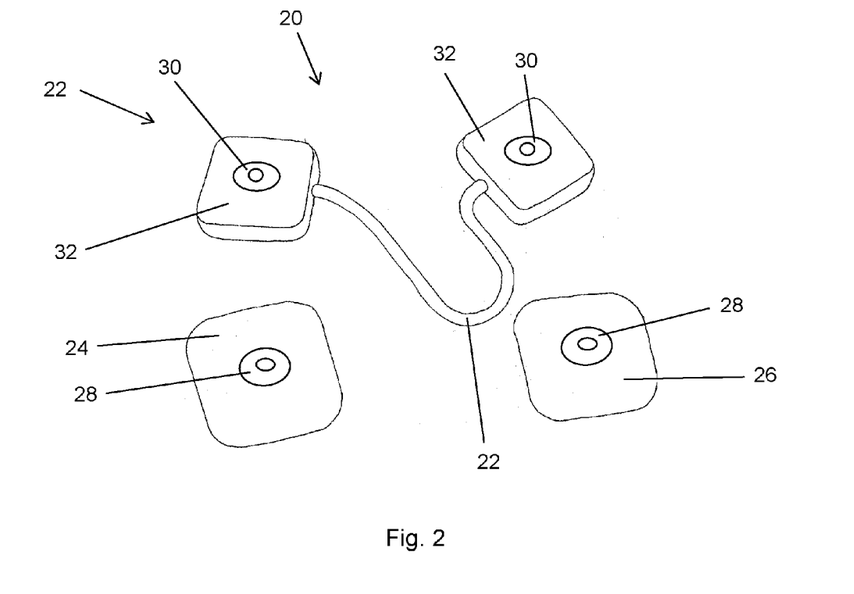
FIG. 2 shows a TENS device and electrodes for use with the TENS device, according to an embodiment.

FIG. 2 shows a system 20 for applying electrical signals to a body part of a subject (patient). The system 20 comprises a medical device 22 for generating electrical signals and first and second electrodes 24, 26 for attachment to the skin of the subject which receive the electrical signals generated by the medical device 22 and transmit them into the subject's body tissue. The system 20 includes first and second magnetic connector assemblies according to embodiments of the invention. Each magnetic connector assembly comprises a first connector part 28 and a second connector part 30, which is connectable to the first connector part such that an electric signal can be transmitted between the first and second connector parts 28, 30. Each of the first connector parts has a first connection surface and each of the second connector parts has a second connection surface. When a first and a second connector part are connected the first and second connection surfaces overlap, partially or completely. This region of overlap will hereafter be referred to as a connection region. The system shown in FIG. 2 is a wireless TENS system, comprising a TENS device and first and second skin-mountable electrodes, although it will be appreciated that the magnetic connector assembly of the invention can be utilized with any medical device-electrode system, and indeed with any system in which a first component needs to be mechanically and electrically coupled to a second component, and with any number of electrodes.

Each magnetic connector assembly is arranged such that the magnetic force between the second connection surface and the first connection surface is weaker in a first part of the connection region than in a second part of the connection region, for example because the magnetic field is weaker in the first part. By introducing a local weakness in the magnetic field the connection force at that location becomes lower and facilitates disconnection. Preferably the first part of the connection region in which the magnetic force is weaker is located at an edge of the connection region. This means that the force required to disconnect the first and second connector parts 28, 30 varies with both location and with the direction in which the force is applied.

Preferably the difference between the magnetic force in the first part of the connection region and the magnetic force in the second part of the connection region is in the range 1 to 10N. Preferably the difference between the magnetic force in the first part of the connection region and the magnetic force in the second part of the connection region is at least 2N.

Advantageously, this means that the a first and second connector parts 28, 30 can be more easily disconnected by applying a separating force to the edge of one or both of the first and second connector parts 28, 30 at or near the first area of the connection region than by applying a force elsewhere (for example applying a perpendicular force to the center of the first and and/or second connector parts, or applying a force in any direction to an edge of the first and/or second connector parts which corresponds to the second area of the connection region). A user wishing to disconnect the first and second connector parts 28, 30 will know where to most effectively apply a separating force (for example by way of a tab or other tactile and/or visible indicator provided on the device housing at a location corresponding to the first area of the connection region), and will therefore find such disconnection to be relatively easy. It is unlikely, however, that a force which is unintentionally applied to the first and/or second connector parts 28, 30 (for example if the subject knocks the medical device by brushing against an item of furniture) would be exerted in the exact place and manner necessary to take advantage of the weaker magnetic force in the first part of the connection region.

Further advantages of providing a local weakness in the magnetic force between the connector parts include making the connector assembly easier to use by subjects who have limited use of their fingers and/or hands, making the connector easier to use when located on difficult to reach body parts where it may be difficult for the subject to exert any significant degree of force, and making the disconnection experience less uncomfortable for the subject when the connector assembly is used with skin-mounted electrodes, since the amount of pulling force transmitted to the adhesive mount of the electrode is reduced as compared to that required to disconnect many prior art connector assemblies commonly used for this application.

Examples of ways in which such a local weakening in the magnetic force between the first and second connector parts 28, 30 can be achieved will be discussed in the following.

In the example the medical device 22 comprises first and second elements 32 connected by a lead 34. Each of the elements 32 is arranged to connect to a respective electrode 24, 26, and so each element 32 includes a second connector part 30. As can be seen from the embodiment of FIG. 3, each element 32 has a housing 34. Preferably this housing is formed of an inexpensive, lightweight and inert material such as a plastics material. Contained within the housing 34 there is a package of electronic components 36 for generating an electrical current, including a battery and a receiver for receiving control signals from a remote control. Below the electronic components 36 is located the second connector part 30. The second connector part 30 is electrically connected to the electronic components 36 by means of a lead, solder connection or any other suitable way of making an electronic connection known to the skilled person, such that an electronic signal generated by the electronic components 36 is transmitted to the second connector part 30. On a bottom surface of element 32 the housing 34 includes a hole sized to accommodate the second connector part 30, such that the bottom surface 38 of second connector part 30 forms part of the bottom surface of element 32. The bottom surface 38 of second connector part 30 is arranged to form an electrical connection with a first connector part 28, and will therefore hereafter be referred to as the second connection surface.

Figure 3:
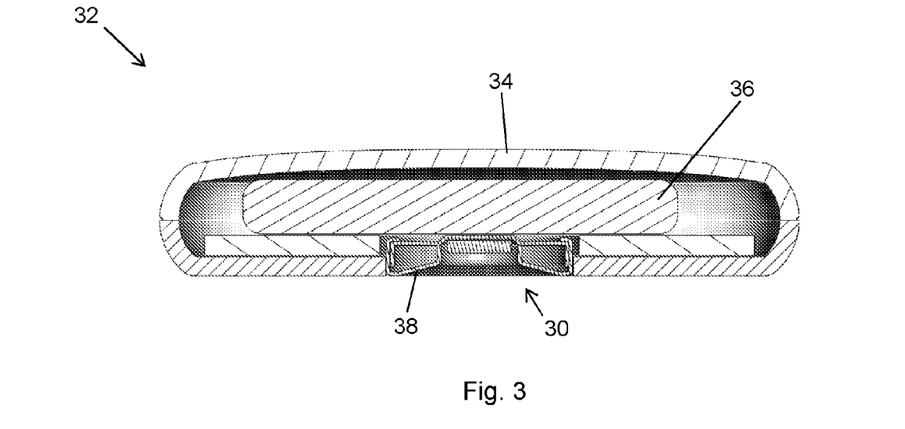
FIG. 3 is a cross-section through a medical device including a second connector part according to an embodiment.

It can be appreciated from FIG. 3 that the second connector part 30 makes a significant contribution to the height of element 32, and it is therefore desirable that second connector part 30 be as thin as possible.

Figure 4:
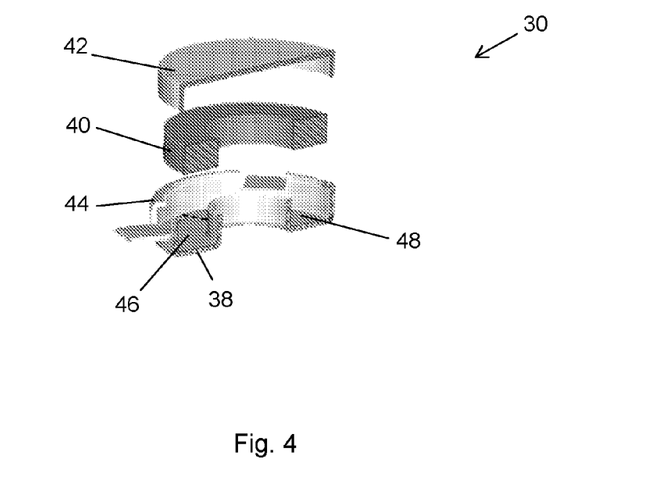
FIG. 4 is an exploded cross-sectional view of a second connector part according to an embodiment.

FIG. 4 illustrates the internal construction of an exemplary second connector part 30 according to an embodiment of the invention. At the heart of second connector part 30 is a magnet 40. Preferably the magnet 40 is ring-shaped. Preferably the magnet 40 is a rare earth magnet, for example a neodymium magnet. It will be appreciated that a neodymium magnet of a given size provides a particularly strong magnetic field as compared to other magnets of the same size, therefore allowing magnet 40 to be very small. According to one example embodiment the diameter of the magnet is less than 17 mm and the thickness of the magnet is less than 3 mm. According to another example the diameter of the magnet is less than 10 mm and the thickness of the magnet is less than 1.5 mm. Other diameters and thicknesses may be used without departing from the scope of the invention, as may other magnetic materials or other shaped magnets. Preferably the magnet should generate a sufficiently strong magnetic field such that the force required to disconnect the first connector part from the second connector part, when applied in a direction perpendicular to the plane of the second connector part, is at least 15N. The magnet may be coated with a layer of electrically conducting material such as nickel.

In some embodiments the magnet may comprise two or more different magnetic materials. The two or more different magnetic materials may generate magnetic fields of differing strengths. In such embodiments, a magnet portion comprising a first, weaker, magnetic material may be located directly above a first area of the second connection surface and a magnet portion comprising a second, stronger, magnetic material may be located directly above a second area of the second connection surface, such that the magnetic field strength at the first area is weaker than the magnetic field strength at the second area. In other alternative embodiments magnet 40 may comprises a plurality of magnets. Each of the plurality of magnets may be of equal strength. Each of the plurality of magnets may be of equal size. Alternatively, some of the plurality of magnets may be stronger than others of the plurality of magnets. In such embodiments the relatively weaker magnets may be located directly above a first area of the second connection surface and the relatively stronger magnets may be located directly above a second area of the second connection surface, such that the magnetic field strength at the first area is weaker than the magnetic field strength at the second area.

In the embodiment shown in FIG. 4, a ring-shaped magnet 40 is encased between a cover 42 and a housing 44, which serve to protect the magnet from becoming damaged during the construction and/or use of the second connector part 30 and/or medical device 22. The cover 42 covers the top surface and outer side wall of the magnet. Cover 42 may be formed from a magnetisable material, for example a ferromagnetic material. Alternatively, the cover 42 may include an electrically insulating material such as a plastics material. Alternatively, cover 42 may include both a non-magnetisable metal and an electrically insulating material. If the cover 42 includes magnetisable material then the resulting encapsulation of the top and sides of magnet 40 in magnetisable material has the effect of concentrating the magnetic field produced by the magnet towards the second connection surface, because the magnetisable material absorbs the magnetic field in other directions. Such encapsulation allows greater magnetic force to be generated by a given size of magnet (thus enabling a smaller magnet to be used). Additionally, the encapsulation of the top and sides of magnet 40 by a cover 42 which includes magnetisable material protects the electronic components 36 from stray field radiation generated by the magnet (i.e. the cover 42 acts as a magnetic shield). If the cover is made of an electrically insulating material then an electrical connection is provided in the cover to allow electrical signals to be transmitted from the electrical components 36 to the connection surface 38.

The housing 44 covers the inner side wall and the bottom surface of magnet 40, and extends upwardly over at least part of the outer side wall around the side wall so that the magnet 40 is fully encapsulated by housing 44 and cover 42. A plurality of tabs 46 (for example three, of which only two are visible in FIG. 4) can be provided to extend radially outwardly from housing 44 to provide a means of fixing the second connecting part 30 in place within element 32. The bottom surface of the housing 44 forms the connection surface 38 by which an electrical connection with the first connecting part 28 is made.

Because the magnet 40 (and the housing 44) are ring-shaped according to this embodiment, a recess is effectively created in the second connection surface 38. This recess may receive a corresponding lug or stud provided on a connection surface of a first connector part. Cooperation between the stud and the recess prevents lateral movement between the first and second connection surfaces. Preferably the stud and the recess are arranged so as to permit relative rotation therebetween when the second connector part is connected to the first connector part. Preferably the stud and recess are circular. Preferably the lug and recess are provided substantially centrally on their respective connection surfaces. Permitting relative rotation between the first connector part and the second connector parts when they are connected helps to ensure that the subject's freedom of movement is not restricted when wearing a TENS device. This is also advantageous in other situations, including for example when skin-mounted electrodes are used for muscle stimulation during physical therapy.

Cooperation between the stud and the recess also has an advantage in facilitating easier location and coupling of the first and second connector parts.

Housing 44 is preferably made of a non-magnetisable material. Housing 44 may be made of a non-magnetisable metal (such as, for example, stainless steel or aluminum). Housing 44 may include a portion of magnetisable material. Alternatively housing 44 may be formed from an electrically and magnetically transparent material (i.e. a material which does not affect the magnetic field) such as a plastics material or a non-magnetisable metal. Housing 44 may be formed partly of an electrically insulating material and partly of an electrically conducting material. If the housing 44 is made entirely of an electrically insulating material then, as mentioned above, an electrical connection is provided to allow electrical signals to be transmitted to the second connection surface 38. If the bottom part of housing 44 is formed of a magnetisable material such as a ferromagnetic material then the magnetic field strength at the connection surface 38 will be less than if the bottom part of housing 44 was formed of a magnetically transparent material, or if housing 44 was not present. Magnetic field strength decreases with distance from the surface of the magnet, thus the thickness of the bottom part of housing 44 will affect the magnetic field strength at the connection surface 38.

In some second connecting parts according to embodiments of the present invention, the magnetic field strength at a first area of the connection surface is weaker than the magnetic field strength at a second area of the connection surface. In the specific example shown in FIG. 4, this is achieved by means of the bottom part of the housing 44 being formed from two different materials. A first housing section 46 is formed from a magnetisable material which will "absorb" the magnetic field and thus create a local weakening of the magnetic field strength. A second housing section 48 is formed from a magnetically transparent material. In some embodiments second housing section 48 substantially comprises an air gap. In some embodiments second housing section 48 comprises a plastics material. In alternative embodiments second housing section 48 comprises a non-magnetisable metal (such as, for example, stainless steel or aluminum). If neither of the first or second housing sections 46, 48 comprises an electrically conducting material then an electrical connection is provided to transmit electrical signals across the housing 44.

In such embodiments the magnetisable material has the effect of absorbing the magnetic field, so the magnetic field strength over the area of the connection surface formed by the first housing section 46 is significantly weaker than the magnetic field strength over the area of the connection surface formed by the second housing section 48 (since this section comprises a magnetically transparent material which does not absorb the magnetic field). Preferably the area of second housing section 48 is greater than the area of first housing section 46.

In alternative embodiments (not illustrated) a similar effect is achieved by forming the whole of the bottom surface of housing 44 from a magnetisable material which absorbs the magnetic field, except for a cut away region in which no material is present. The cut-away region may correspond to the second housing section 48 of the embodiment of FIG. 4. In such alternative embodiments the second connection surface 38 is formed by the bottom surface of magnet 40 in the cut-away region where no housing material is present.

Figure 5:
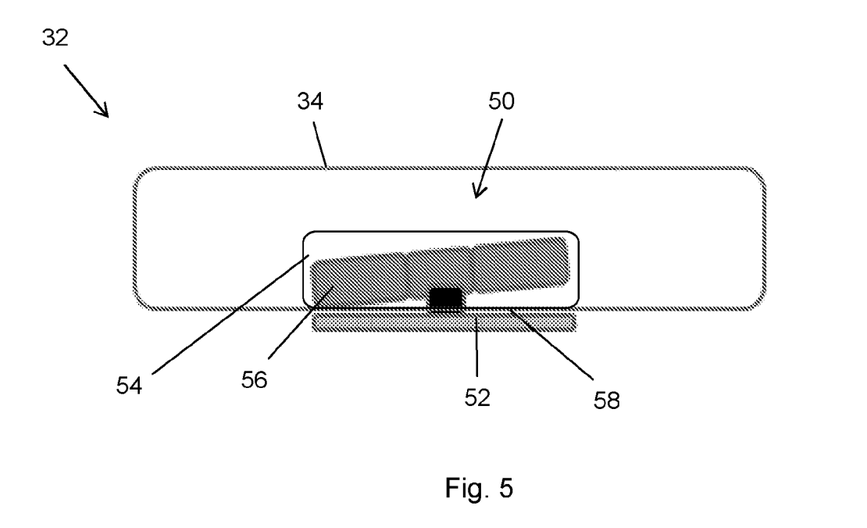
FIG. 5 shows a second connector part according to a first alternative embodiment.

FIG. 5 shows a second connector part 50 according to a further alternative embodiment of the invention. The second connector part 50 is shown connected to a connection surface 52 of a first connecting part. As with the embodiment shown in FIG. 4, second connector part 50 comprises a magnet 56 encased in a housing 54 such that the bottom part of housing 54 forms a second connection surface 58 for forming an electrical connection with connection surface 52. The housing 54 is formed from a magnetically transparent, electrically insulating material, such as a plastics material. The housing 54 includes conducting means (not shown) for transmitting electrical signals from a medical device to which second connector part 50 is connected to second connection surface 52. Alternatively the housing 54 may be formed from a non-magnetisable metal, in which case separate conducting means are not necessary. The housing 54 is configured, for example by having walls that are of uneven thickness, such that the magnet 56 is disposed at an angle with respect to the second connection surface 58. Consequently the far left hand side (as seen in FIG. 5) of magnet 56 is very close to connection surface 58, whereas the far right hand side of magnet 56 is relatively much further away from connection surface 58. This has the effect that the magnetic field strength at the far left hand side of connection surface 58 is significantly stronger than the magnetic field strength at the far right hand side of connection surface 58. As such, the first and second connector parts are arranged such that the magnetic force between the first and second connection surfaces is substantially weaker in a first part of the connection region than in a second part of the connection region.

Figure 6:
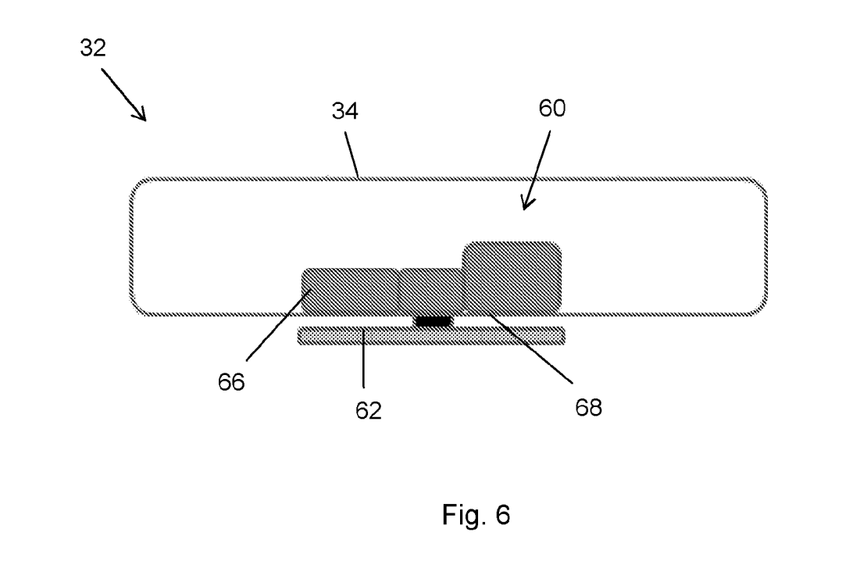
FIG. 6 shows a second connector part according to a second alternative embodiment.

FIG. 6 shows a second connecting part 60 according to a further alternative embodiment of the invention. The second connecting part 60 is shown connected to a connection surface 62 of a first connecting part. Second connecting part 60 comprises a magnet 66. Second connecting part 60 does not include a housing around magnet 66, thus the bottom surface of magnet 66 forms a second connection surface 68 for forming an electrical connection with connection surface 62. Electrical signals may be transmitted directly through magnet 66, or alternatively magnet 66 may be provided with an electrically conductive coating though which electrical signals can be transmitted. The thickness of the magnet 66 is uneven, such that the right hand side (as seen in FIG. 6) of magnet 66 is thicker than the left hand side of magnet 66. This has the effect that the magnetic field strength at the right hand side of connection surface 68 is stronger than the magnetic field strength at the left hand side of connection surface 68. According to one example the thicker portion of magnet 66 comprises at least half of magnet 66. According to another example the thicker portion of magnet 66 comprises at least two-thirds of magnet 66. It is noted that other ratios of thicker portion to thinner portion are also intended to fall within the scope of the invention. Preferably the thickness of the thicker portion of magnet 66 is not greater than 3 mm. As such, the arrangement of FIG. 6 also provides first and second connector parts that are arranged such that the magnetic force between the first and second connection surfaces is substantially weaker in a first part of the connection region than in a second part of the connection region.

Further alternative embodiments (not illustrated) are possible in which the second connection surface of the second connector part comprises a protrusion extending perpendicularly to the second connection surface. It will be appreciated that when such a second connector part is used with a first connector part having a substantially flat first connection surface, the protrusion has the effect of creating a gap between the second connection surface and the first connection surface in the area surrounding the protrusion when the two connector parts are connected. The effect of this gap is that the separation between the magnet in the second connector part and a magnetisable target in the first connector part on which the magnetic field generated by the magnet acts, is greater in the area surrounding the protrusion than elsewhere in the connection region. Since magnetic field strength decreases with distance, the magnetic force between the first and second connector parts will consequently be less in the area surrounding the protrusion. It will be appreciated that the same effect is created if the protrusion is formed on the first connection surface of the first connector part, and the second connection surface of the second connector part is substantially flat.

Figure 7:
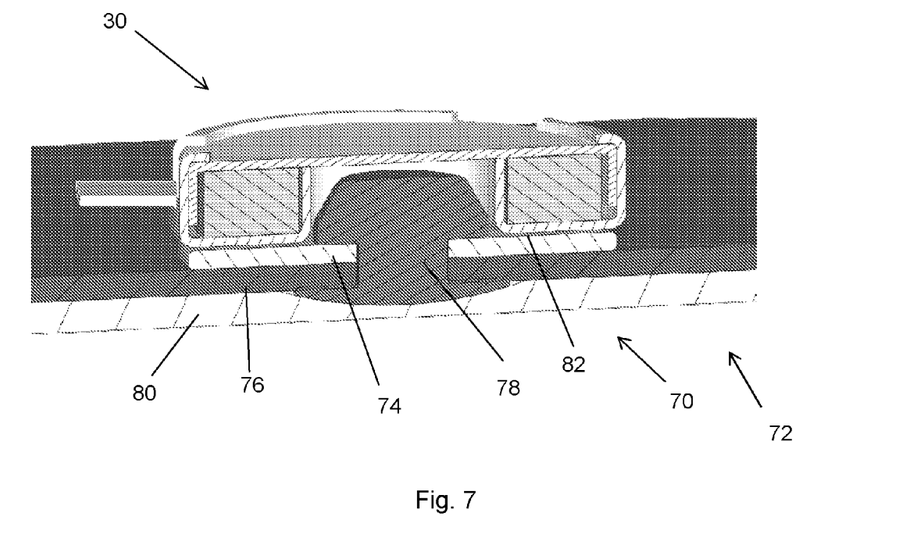
FIG. 7 shows a cross-section through a second connector part according to an embodiment, connected to a first connector part according to an embodiment.

FIG. 7 shows the second connector part 30 of FIG. 4 connected to a first connector part 70 (the medical device to which the second connector part 30 is attached has been omitted for clarity purposes). First connector part 70 forms part of a skin-mountable electrode 72, the construction of which can be more easily seen from FIG. 8. Electrode 72 comprises a target 74 attached to a layer of flexible material 76 by a pin 78. The layer of flexible material 76 may comprise any suitable material, for example a fabric or a plastics material. If the material forming the layer of flexible material is not electrically conductive, then conducting means are provided to transmit electrical signals through this layer. An adhesive layer 80 is provided on the bottom surface of the layer of flexible material 76 to facilitate attachment to skin. Preferably the adhesive layer 80 comprises a hydrogel, although any suitable adhesive which permits the conduction of electronic signals may be used. In some embodiments a conductive film (not shown) comprising, for example, carbon, silver or aluminum, is sandwiched between the layer of flexible material 76 and the adhesive layer 80. The effect of this conductive film is to spatially distribute the electrical current over the area of the electrode and thus avoid severe variances in the current density (i.e. "hot spots" which can cause discomfort and possibly even skin damage) delivered to the subject during electrical stimulation.

Figure 8:
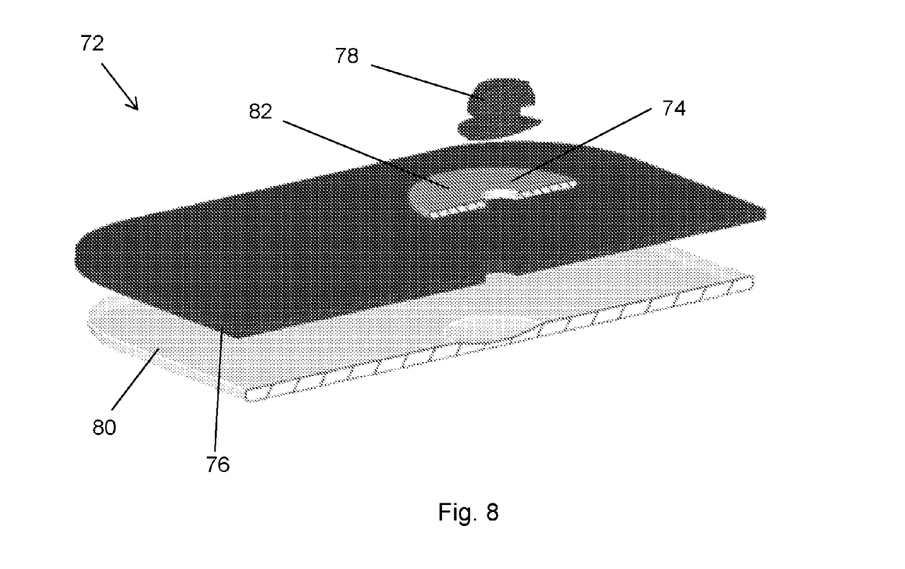
FIG. 8 shows an exploded cross-sectional view of an electrode including a first connector part according to an embodiment.

The top surface of target 74 forms a first connection surface 82 which is arranged to form an electrical connection with the second connection surface 38 of second connector part 30. A pin 78 passes through a hole formed in the layer of flexible material 76 and a hole formed in the target 74 such that an end portion of pin 78 protrudes from the top surface of the target 74. The protruding end portion of the pin 78 preferably has a larger diameter than the diameter of the hole in target 74, so that pin 78 fastens the layer of flexible material 76 and the target 74 together in a sandwich arrangement. The pin 78 may be formed from any suitable material known to the skilled person, for example metal or a plastics material. If the pin 78 is metal then it may provide a means of transmitting electrical signals between the first connection surface 82 and the adhesive layer 80. In some embodiments the pin material is a carbon loaded plastic which is conductive and can transmit electrical signals. It will be appreciated that other ways of fixing the target 74 to the layer of flexible material 76 are possible. For example the target 74 may be glued to the layer of flexible material 76. Alternatively, a rivet may be used to fix target 74 to layer of flexible material 76.

As can be seen from FIG. 7, the protruding end portion of pin 78 forms a stud on first connection surface 82. This stud engages with a corresponding recess in second connection surface 38 so as to prevent lateral movement between the first and second connector parts 30, 70. The stud and recess are shaped so as to permit relative rotation therebetween (in this embodiment both stud and recess are circular, although it will be appreciated that other arrangements, for example a circular stud and a square recess, would also permit such rotation). It will be appreciated that other arrangements for preventing lateral movement between the first and second connector parts 30, 70 are possible. For example, one or more recesses may be formed in the surface of the target 74, which are arranged to mate with one or more protrusions formed on a connection surface of a second connector part. Either of the connection surfaces may comprise a raised peripheral rim, arranged to surround the edge of the other connection surface. In this case the main area of both connection surfaces may be substantially flat.

The target 74 forms the majority of the first connection surface 82, and is therefore able to couple electrically and magnetically with a connection surface on a second connector part. To this end, preferably the target comprises an electrically conductive magnetisable material, such as a ferromagnetic material. Alternatively, however, the target could comprise a non-electrically conductive magnetic or magnetisable material coated with an electrically conductive material. Preferably the surface area of the target 74 (and therefore of the first connection surface 82) is substantially the same size and shape as the connection surface of the second connector part to which it is intended to be connected.

As described above, in some embodiments of the invention the second connector part includes a connection surface and/ or magnet which is asymmetrically shaped such that the magnetic field strength at a first area of the connection surface is weaker than the magnetic field strength at a second area of the connection surface (such as the embodiments shown in FIGS. 4, 5 and 6). It will be appreciated that second connector parts according to such embodiments can be connected with substantially symmetric first connector parts (such as those known in the art as part of conventional magnetic connection systems). Such connection of an asymmetric second connector part with a conventional first connector part will result in the magnetic force between the first connection surface of the first connector part and the second connection surface of the second connector part being substantially weaker in a first part of the connection region than in a second part of the connection region, and thus falls within the scope of the present invention. However; the present invention also envisages use of an asymmetric first connector part, which may be used with a conventional, substantially symmetric second connector part to achieve the effect of the invention. Embodiments of the invention in which the first connector part is asymmetric (i.e. the first connection surface and/or the target is shaped such that, when exposed to a substantially uniform magnetic field, the magnetic force experienced by a first area of the connection surface is substantially weaker than the magnetic force experienced by a second area of the connection surface) will now be described.

Figure 9:
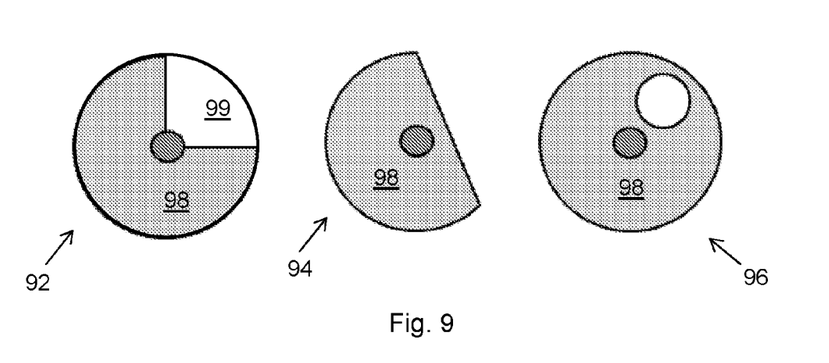
FIG. 9 shows three exemplary targets for a first connector part according to alternative embodiments.

FIG. 9 shows examples of three different targets 92, 94, 96 which can be used in place of target 74 in the first connecting part 70 shown in FIG. 7 in some embodiments of the invention. Each of the targets 92, 94, 96 comprises a ferromagnetic metal 98 which becomes magnetized in the presence of a magnetic field. However, the shape of each of the targets 92, 94, 96 is irregular: target 92 is a disc from which a quarter sector is missing, target 94 is a disc from which a segment is missing, and target 96 is a disc which has an off-center circular hole cut through it. In target 92 the sector which does not comprise ferromagnetic material is formed from a magnetically transparent material 99, such as a plastics material or a non-magnetisable metal, or alternatively may be left blank. In targets 94 and 96, no material is present in the missing segment and hole (although the missing segment and hole could also comprise a magnetically transparent material). The effect of the construction of the targets 92, 94 and 96 is to weaken the magnetic force between the target and a magnet in the region of the target which does not comprise ferromagnetic material. Preferably the region which does not contain ferromagnetic material 98 is located at or near an edge of the target, such that the magnetic force experienced at one side of the target (corresponding to the region not comprising ferromagnetic material 98) is substantially weaker than the magnetic force experienced at an opposite side of the target. It is noted that other arrangements can be provided for realizing a target 74 that cooperates with a magnet to create a weaker magnetic field in one area compared with a magnetic field in another area. For example a cut-out can be formed in the ferromagnetic material 98, the cut-out being in the form of a word or visual indication which acts to identify the weaker area of magnetic field, and hence the area where the connector should be detached.

Figure 10:
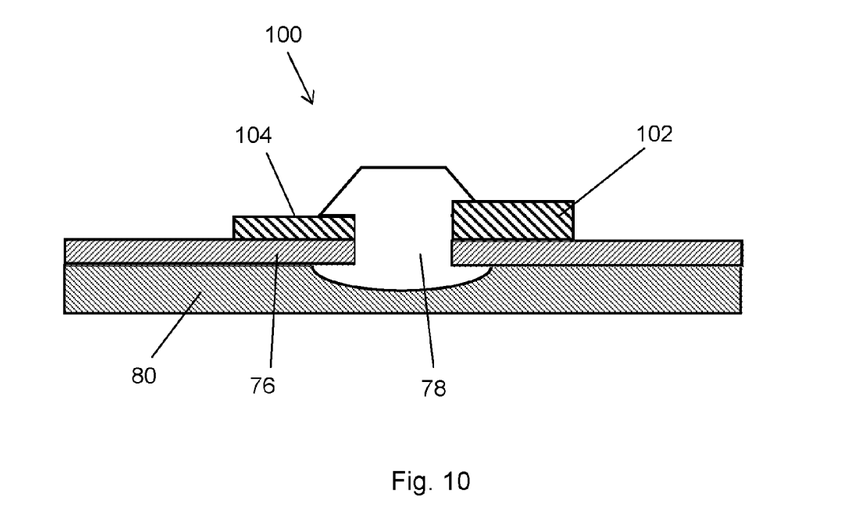
FIG. 10 shows a first connector part according to a further alternative embodiment.

FIG. 10 shows a first connector part 100 comprising a further alternative target 102. The target 102 comprises a disc of ferromagnetic metal 98. However, the target 102 includes a portion which is less thick than the rest of the target (shown on the left in FIG. 10). The effect of this thinner portion of target 102 is to weaken the magnetic force between the target and a magnet in the region of the thinner portion. Preferably the thinner portion is located at or near an edge of the target, such that the magnetic force experienced at the side of the target which includes the thinner portion is substantially weaker than the magnetic force experienced at an opposite side of the target. It will be appreciated that the first connection surface 104 of the first connector part 100 is uneven due to the uneven thickness of the target 102, which may be undesirable for some applications of the invention. Thus, in some embodiments (not illustrated) the thinner portion of target 102 is covered with a layer of any suitable magnetically transparent material so as to create a flat connection surface across the whole area of the target.

In the embodiments of the invention described above with reference to FIGS. 9 and 10, the first connector part is asymmetric in the sense that it includes a connection surface and/or target shaped such that, when exposed to a substantially uniform magnetic field, the magnetic force experienced by a first area of the connection surface is substantially weaker than the magnetic force experienced by a second area of the connection surface. It will be appreciated that first connector parts according to such embodiments can be connected with substantially symmetric second connector parts (such as those known in the art as part of conventional magnetic connection systems). Such connection of an asymmetric first connector part with a conventional second connector part will result in the magnetic force between the first connection surface of the first connector part and the second connection surface of the second connector part being substantially weaker in a first part of the connection region than in a second part of the connection region, and thus falls within the scope of the present invention.

It is also possible, within the scope of the present invention, to use an asymmetric first connector part (such as the first connector parts of FIGS. 9 and 10) in connection with an asymmetric second connector part (such as the second connector parts of FIGS. 4 to 7). It will be appreciated that in such embodiments it is necessary to arrange the first and second connection surfaces in a particular orientation such that the regions of the connecting surfaces at which the magnetic force is weaker are substantially aligned. Since it is generally desirable for the first and second connection surfaces to be able to rotate relative to each other, such embodiments will be less preferred for most applications.

Although the embodiments described above assume that the first connector part is attached to an electrode and the second connector part is attached to the medical device, it will be appreciated that this arrangement may be reversed. However, for many applications it is common practice for the electrodes to be disposable. It is therefore desirable that the construction of the electrodes be as simple and inexpensive as possible. Since the magnet in the second connector part will typically be significantly more expensive than the magnetisable target in the first connector part, for such applications it is advantageous to provide the second connector part in the medical device and the first connector part on the electrode.

It is noted that the various configurations of the first connector part and the second connector part may be used in any combination.

Although the invention has been described above as being preferably for use in connecting a TENS device to electrodes mounted on the skin of a subject, it will be appreciated that the invention can advantageously be used with any type medical device which uses electrodes. For example, a magnetic connector assembly according to the invention could be used with a device for monitoring physiological parameters such as heart rate, or electrical activity in a particular body part, or with a device with delivers stimulation, including devices for stimulating muscles and or nerves, or for transcranial magnetic stimulation. The invention could also be used in applications where one of the connector parts is at least partially implanted into the subject, for example to connect to a cochlear implant. Although the invention is primarily concerned with medical applications, it will be appreciated that the invention can advantageously be used in any application where two electronically connectable components must be capable of easy connection and disconnection.

There is therefore provided a magnetic connector assembly in which the magnetic force between first and second connector parts of the assembly is weaker at a first region of connection than at a second region of connection so as to facilitate separation of the first and second connector parts.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A first connector part connectable to a second connector part such that an electrical signal may be transmitted therebetween, the first connector part comprising:
   a target comprising magnetizable material;
   a first connection surface, disposed on the target, arranged to be engageable with a corresponding second connection surface on a second connector part such that an electrical signal can be transmitted between the first connection surface and the second connection surface; and
   wherein the first connector part is characterized by being arranged such that, when exposed to a uniform magnetic field, the magnetic force experienced by a first area of the connection surface is substantially weaker than the magnetic force experienced by a second area of the connection surface,
   wherein the first area of the connection surface is located adjacent to an edge of the connection surface,
   and wherein one of the first and second connection surfaces comprises a protrusion arranged to engage with a corresponding recess on the other one of the first and second connection surfaces, wherein the engagement substantially prevent relative lateral movement between the first and second connection surfaces whilst permitting relative rotation thereof, wherein the rotation between the first connector part and the second connector part is permitted when both the said connector parts are engaged with respect to each other.

2. The first connector part of claim 1, wherein a surface of the target forms at least part of the connection surface.

3. The first connector part of claim 1, wherein the target additionally comprises a non-magnetizable material, and wherein the first area of the first connection surface corresponds to the part of the target which comprises a non-magnetizable material and the second area of the connection surface corresponds to the part of the target which comprises a magnetisable material.

4. The first connector part claim 1, wherein the shape of the portion of the target which comprises magnetizable material is asymmetric with respect to the center of the first connection surface, such that the amount of magnetizable material contained in the volume of the first connector part, associated with a first side of the first connection surface is greater than the amount of magnetizable material, contained in the volume of the first connector part, associated with the second side of the first connection surface, and wherein the first area of the first connection surface is contained within the second side.

5. The first connector part of claim 1, wherein the portion of the target which comprises magnetizable material has a non-uniform thickness in a direction perpendicular to the connection surface, such that the amount of magnetizable material contained in the volume of the first connector part, associated with a first side of the first connection surface is greater than the amount of magnetizable material contained in the volume of the first connector part, associated with the second side of the first connection surface, and wherein the first area of the first connection surface is contained within the second side.

6. The first connector part of claim 1, further comprising a layer of flexible material having an attachment surface arranged to attach to a body tissue of a subject such that an electrical signal may be transmitted between the attachment surface and the body tissue; wherein at least part of the attachment surface is electrically connected to the first connection surface, and wherein the layer of flexible material and the target are fastened together in a sandwich arrangement by a pin.

7. The second connector part of claim 1, wherein the magnetic material comprises neodymium.

8. A second connector part connectable to a first connector part such that an electrical signal may be transmitted therebetween, the second connector part comprising:
a second connection surface arranged to be engageable with a corresponding first connection surface on a first connector part such that an electrical signal can be transmitted between the second connection surface and the first connection surface; and
a magnet comprising magnetic material;
wherein the second connector part is characterized by being arranged such that the magnetic field strength at a first area of the second connection surface is weaker than the magnetic field strength at a second area of the second connection surface,
and wherein one of the first and second connection surfaces comprises a protrusion arranged to engage with a corresponding recess on the other of the first and second connection surfaces, wherein the engagement substantially prevent relative lateral movement between the first and second connection surfaces whilst permitting relative rotation thereof, wherein the rotation between the first connector part and the second connector part is permitted when both the said connector parts are engaged with respect to each other.

9. The second connector part of claim 8, wherein a first portion of the magnet which corresponds to the second area of the second connection surface comprises the magnetic material and a second portion of the magnet which corresponds to the first area of the second connection surface comprises a further, different, magnetic material, and wherein the magnetic field generated by the magnetic material is stronger than the magnetic field generated by the further magnetic material.

10. The second connector part of claim 8, wherein shape and/or location of the magnet is asymmetric with respect to the center of the second connection surface such that magnetic field strength exerted by the magnetic material contained in the volume of the second connector part associated with a first side of the second connection surface is greater than magnetic field strength exerted by the magnetic material contained in the volume of the second connector part associated with the second side of the second connection surface, and wherein the first area of the second connection surface is contained within the second side.

11. The second connector part of claim 8 further comprising a magnet housing which at least partially surrounds the magnet and forms at least part of the second connection surface, wherein the magnet housing partially comprises a magnetically transparent material and partially comprises a magnetizable material such that the part of the magnet housing which comprises a magnetizable material forms the first area of the second connection surface and the part of the magnet housing which comprises a magnetically transparent material forms the second area of the second connection surface.

12. The second connector part of claim 11, wherein the magnet housing is shaped such that the separation between the magnet and the second connection surface is greater at a first point corresponding to the first area of the second connection surface than at a second point corresponding to the second area of the second connection surface.

13. A transcutaneous electrical nerve stimulation apparatus comprising: a first connector part connectable to a second connector part such that an electrical signal may be transmitted therebetween, the first connector part comprising:
a target comprising magnetizable material;
a first connection surface, disposed on the target, arranged to be engageable with a corresponding second connection surface on a second connector part such that an electrical signal can be transmitted between the first connection surface and the second connection surface; and
wherein the first connector part is characterized by being arranged such that, when exposed to a uniform magnetic field, the magnetic force experienced by a first area of the connection surface is substantially weaker than the magnetic force experienced by a second area of the connection surface,
wherein the first area of the connection surface is located adjacent to an edge of the connection surface,
and wherein one of the first and second connection surfaces comprises a protrusion arranged to engage with a corresponding recess on the other one of the first and second connection surfaces, wherein the engagement substantially prevent relative lateral movement between the first and second connection surfaces whilst permitting relative rotation thereof, wherein the rotation between the first connector part and the second connector part is permitted when both the said connector parts are engaged with respect to each other.

* * * * *